United States Patent [19]
Malcolm et al.

[11] Patent Number: 5,531,712
[45] Date of Patent: Jul. 2, 1996

[54] SURGICAL SUCTION REGULATOR VALVE

[76] Inventors: Roger J. Malcolm, 920-C Calle Negocio, San Clemente, Calif. 92672; Kevin T. Foley, 2771 Hunter Forrest, Germantown, Tenn. 38138

[21] Appl. No.: 316,117

[22] Filed: Sep. 30, 1994

[51] Int. Cl.⁶ .................................................. A61M 5/00
[52] U.S. Cl. .......................... 604/247; 604/280; 251/208; 137/505.39; 137/513.3
[58] Field of Search ........................... 137/505.39, 513.3, 137/514.7, 515.35; 604/296, 9, 30, 45, 247, 264, 280, 320, 323, 324, 335, 65, 902; 251/88, 180, 181, 186, 188, 192, 208, 264, 304, 309, 903

[56] References Cited

U.S. PATENT DOCUMENTS

| | | |
|---|---|---|
| 3,565,076 | 2/1971 | Kadan . |
| 3,624,821 | 11/1971 | Henderson . |
| 4,013,076 | 3/1977 | Puderbaugh . |
| 4,356,823 | 11/1982 | Jackson . |
| 4,676,779 | 6/1987 | Mayoral . |
| 4,685,654 | 8/1987 | Hu .......................................... 604/246 |
| 4,699,138 | 10/1987 | Behrstock . |
| 4,729,765 | 3/1988 | Eckels . |
| 4,741,326 | 5/1988 | Sidall et al. . |
| 4,909,277 | 3/1990 | Vandiver ................................. 251/208 |
| 5,000,175 | 3/1991 | Pue . |

*Primary Examiner*—Corrine M. Maglione
*Assistant Examiner*—N. Kent Gring
*Attorney, Agent, or Firm*—Henri J. A. Charmasson; John D. Buchaca

[57] ABSTRACT

A relief valve for regulating the operation of a surgical suction device comprises a plunger adjustably screwable into a fluid escape channel. A conical tip at the end of the plunger is shaped and dimensioned to progressively obstruct an escape port. Longitudinal grooves along the threaded walls of the plunger provide a passage for the fluid from or toward the escape port.

11 Claims, 1 Drawing Sheet

SURGICAL SUCTION REGULATOR VALVE

FIELD OF THE INVENTION

This invention relates to relief valves in general, and more particularly to surgical suction device regulators which can be installed in series between a suction tube and a vacuum source.

BACKGROUND OF THE INVENTION

During the course of a surgical operation on a patient, it is often necessary to remove from the site of the operation various body fluids, including blood, which tend to collect there. During childbirth, it is often necessary to remove meconium from the newborn using an intrapartum nasopharyngel suction device. In either case, the suction probe or catheter is usually connected to a pump or other type of vacuum source by means of a flexible tube. It has been found convenient to install a relief valve between the suction probe and the pump in order to control the amount of vacuum applied to the probe. Such a suction control usually consists of a valve which can be adjusted to admit a certain flow of ambient air into the tube, thus, reducing the suction force at the probe.

In some suction devices, the air intake of the regulating valve is controlled by the operators positioning a finger over the air-intake as disclosed in U.S. Pat. No. 5,000,175 Pue. Such a device, must be continuously handled by the operator. Moreover, should the operator drop the device, the maximum rate of ambient air is admitted, thus, reducing or completely interrupting the suction.

Other medical suction control devices such as the one disclosed in U.S. Pat. No. 4,356,823 Jackson offer only a limited range of vacuum adjustments, and no way to adjustably stabilize the setting of the air-intake.

The invention is a result of a search for a more practical type of surgical suction regulating device which does not require continuous handling by the operator, and can be accurately and permanently set to an optimal air flow intake rate.

SUMMARY OF THE INVENTION

The principal and secondary objects of the invention are to provide a simple, yet practical relief valve, to be placed in series between a surgical suction catheter and a suction pump or other type of vacuum source, that can be accurately adjusted, and can maintain its setting unattended. It is also an object of the invention that the suction regulator valve be operable with one hand, be so simple and inexpensive that it can be disposed of after a single use, and be made of such material that can be conveniently sterilized with gamma rays.

These and other objects are achieved by means of a suction regulator valve made of a surgical thermal plastic wherein the regulating mechanism uses a plunger screwable into an air intake channel, and having a precise control knob that can be manipulated between the thumb and the index finger while the body of the valve is held between the palm and the other fingers.

DESCRIPTION OF THE PREFERRED EMBODIMENT OF THE INVENTION

Figure 1:
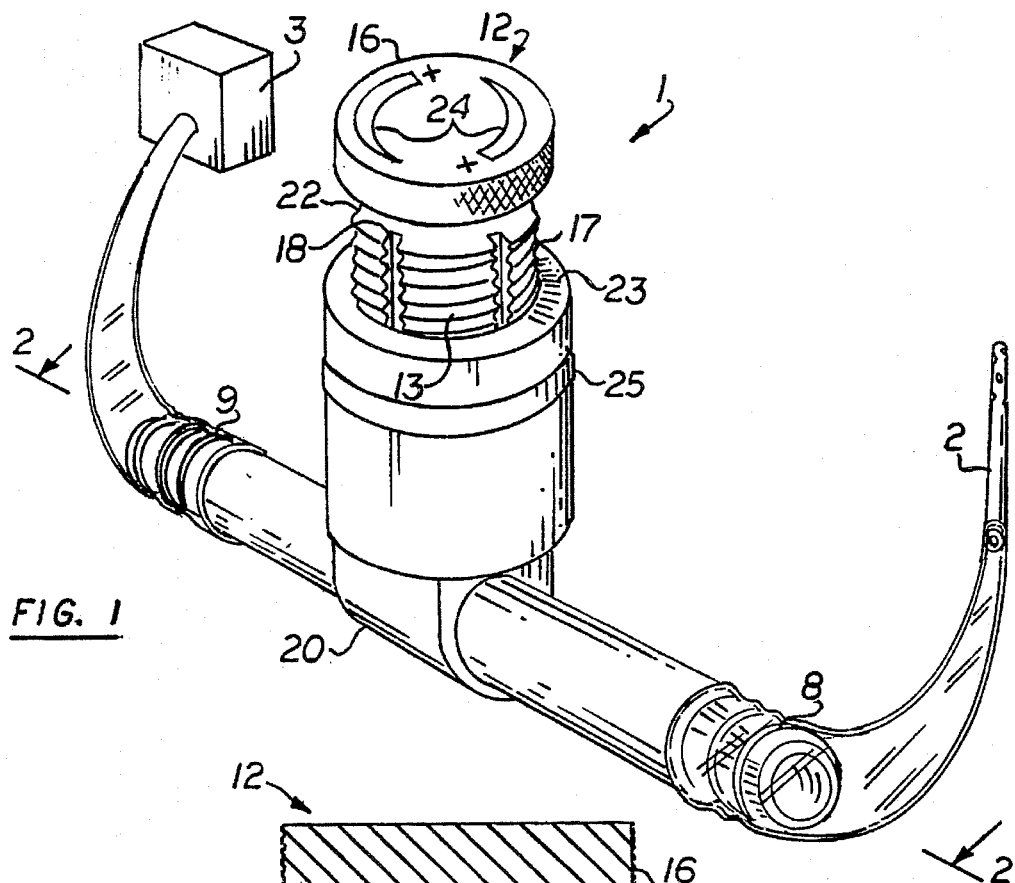
FIG. 1 is a perspective view of a suction regulator valve according to the invention.
Figure 2:
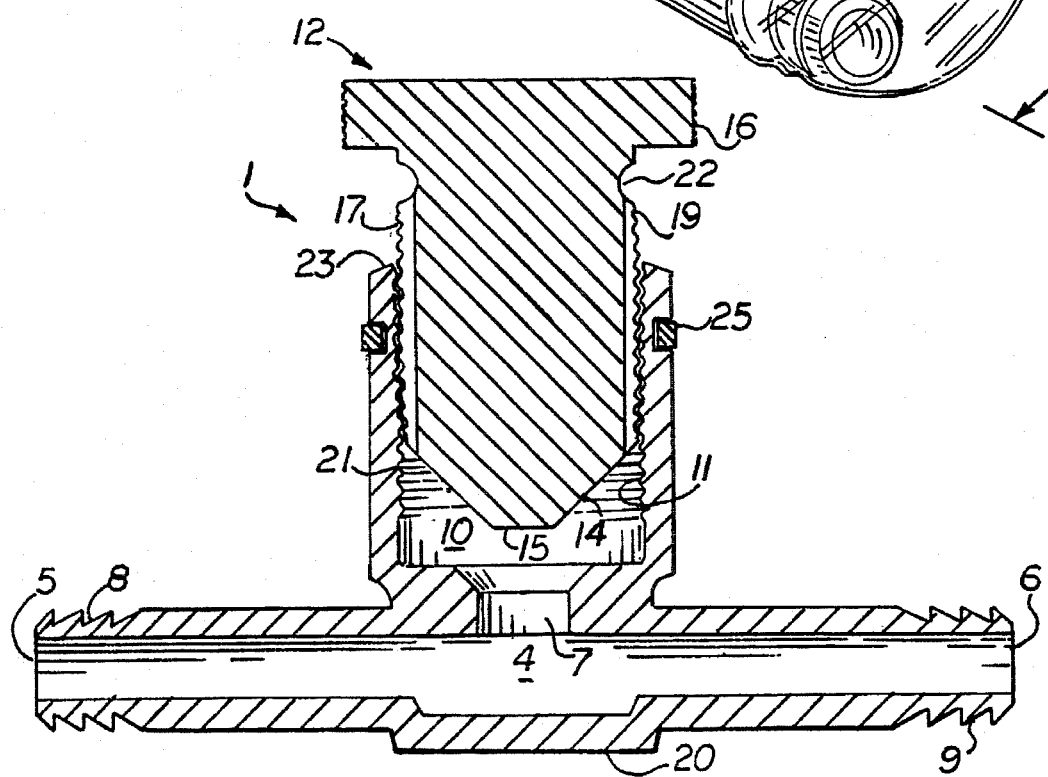
FIG. 2 is a cross-sectional view thereof taken along line 2—2 of FIG. 1.

Referring now to the drawing, there is shown a suction regulator valve 1 specifically designed to be installed in series between a surgical suction tube 2 and a source of vacuum 3.

The suction tube may be part of a surgical meconium aspirator, a surgical wound fluid remover, or other medical aspiration devices. The source of vacuum is usually a pump such as, for example, the medical aspirator disclosed in U.S. Pat. No. 4,676,779 Mayoral. It should be understood that the invention may apply to many kinds of relief valves used in connection with a multiplicity of fluid-carrying conduits either for gases or liquids.

The valve comprises a body 20 defining an internal chamber or passageway 4, and having an inlet port 5 an exit port 6 and an escape relief port 7. The inlet and exit ports have tubular feedings 8 and 9 shaped and dimensioned for engagement into flexible plastic tubes.

The relief port 7 leads into a cylindrical channel 10 having a threaded internal wall 11. A plunger 12, having external dimensions commensurate with the inner dimension of the channel 10 and peripheral threads 13 compatible with the threaded wall 11 of the channel, is adjustably screwed into the channel. The distal end of the plunger 12 has a conical section 14 which tapers down to a tip 15 sized and dimensioned to penetrate and obstruct the relief port 7 when the plunger is fully engaged into the channel 10. At the opposite, proximal end of the plunger, a knurled, circular knob 16 can be manipulated between the thumb and index finger to adjust the relief port aperture while the body of the valve is held between the palm and the other fingers. This allows a one-hand operation of the device. A set of longitudinal grooves 17, 18, and 19 are cut down the side of the plunger perpendicularly to the thread 13 from a largest portion 21 of the conical section 14 to a peripheral, circular groove 22 separating the threaded wall of the plunger 13 from the knob 16. The radial depths of the circular groove is at least as large as the radial depth of the longitudinal grooves. The plunger is dimensioned to keep the circular groove above the rim 23 of the circular channel so that a passageway is always open between the lower part of the channel surrounding the relief port 7 and the outside, regardless of the position of the plunger within the channel.

Threads 11 are fine enough to prevent the plunger 12 from rotating freely when the knob 16 is not being held. Accordingly, should the regulator valve be dropped or left unattended, the air intake aperture will not change.

Markings 24 on the top surface of the knob 16 indicate the turning direction for increasing or decreasing the air flow.

The device is injection molded out of a medically suitable thermal plastic such as a nylon polycarbonate. This type of material allows sterilization by irradiation with gamma rays. Due to its simplicity and ease of fabrication, the valve can be disposed of after a single use. In order to prevent its reuse after sterilization by heat, one or more rings 25 of heat-shrinkable material are embedded into the wall of the channel or the threaded surface of the plunger. The shrinking of such rings under the heat of an autoclave would distort the threads along the internal wall 11 and prevent any adjustment of the device. Alternately, or in addition to the heat-shrinkable rings, the outer surface of the valve can be marked with the notice "Contaminated" using a heat-sensitive pigment. Alternately the notice can be covered with a film that vaporizes under heat, revealing the warning word.

Heat-shrinkable materials are well-known to the art, and are routinely used to make shrinkable tubing used in the fabrication of electronic cables. Heat-sensitive solutions, i.e., solutions that turn color in response to temperature change are also well-known to the art and are used to indicate overheating in certain delicate electronic instruments. Certain resins can be formulated to vaporate under a precise temperature range.

The valve can also be constructed so that once the plunger 12 has been engaged into the channel 10, a snapping barrier interlocks the two elements and prevent their separation while allowing full range of adjustment. Accordingly, the unit cannot be disassembled for sterilization and reuse.

While the preferred embodiment of the invention has been described, modifications can be made and other embodiments may be devised without departing from the spirit of the invention and the scope of the appended claims.

What is claimed is:

1. A relief valve for installation in series with a fluid-carrying conduit, said valve comprising:

a hollow body having an intake port, an exit port, and relief port, and means for adjustably closing said relief port; wherein said means for adjustably closing comprises a cylindrical channel having internal threads; and a cylindrical plunger commensurate with said channel having first and second opposite ends and having peripheral threads shaped and dimensioned to match said internal threads and at least one longitudinal slot across said threads along a side of said plunger, said plunger being adjustably engaged into said channel.

2. The relief valve of claim 1, wherein said plunger further comprises a conical section at said first end proximate to said relief port, said conical section tapering down to a circular tip shaped and dimensioned to close said relief port when said plunger is moved through said channel toward said relief port.

3. The relief valve of claim 2, wherein said longitudinal slot extends across said peripheral threads and along a largest portion of said conical section proximate to said peripheral threads.

4. The relief valve of claim 3, wherein said plunger further comprises a knob at said second end opposite said first end.

5. The relief valve of claim 4, wherein said plunger further comprises a circular, peripheral groove between said peripheral threads and said knob, said groove being at least as radially deep as said longitudinal slot.

6. The relief valve of claim 5 which further comprise means for distorting a portion of said thread when said valve is subject to a sterilizing heat.

7. The relief valve of claim 6, wherein said means for distorting include a heat-shrinkable ring circumferentially embedded into a wall of said body surrounding a portion of said channel.

8. The relief valve of claim 5 which further comprise a warning legend applied to said body within a heat-sensitive medium.

9. The relief valve of claim 5 which further comprises a warning legend applied to said body, and a film of vaporizable material covering said legend.

10. An adjustable surgical suction device which comprise:

a vacuum source;

a fluid carrying conduit;

a relief valve; and a suction tube, wherein said relief valve is connected in series between said suction tube and said vacuum source;

wherein said relief valve comprises:

a hollow body having an intake port, an exit port, and relief port, and means for adjustably closing said relief port; wherein said means for adjustably closing comprises a cylindrical channel having internal threads; and a cylindrical plunger commensurate with said channel having first and second opposite ends and having peripheral threads shaped and dimensioned to match said internal threads and at least one longitudinal slot across said threads along a side of said plunger, said plunger being adjustably engaged into said channel;

wherein said plunger further comprises a conical section at said first end proximate to said relief port, said conical section tapering down to a circular tip shaped and dimensioned to close said relief port when said plunger is moved through said channel toward said relief port;

wherein said longitudinal slot extends across said peripheral threads and along a portion of said conical section proximate to said peripheral threads;

wherein said plunger further comprises:

a knob at said second end; and a circular, peripheral groove between said peripheral threads and said knob, said groove being at least as radially deep as said longitudinal slot.

11. The relief valve of claim 6, wherein said means for distorting include a heat-shrinkable ring circumferentially embedded around said side of said plunger.

* * * * *